United States Patent
Baughman et al.

(10) Patent No.: US 8,856,061 B2
(45) Date of Patent: Oct. 7, 2014

(54) USER EXPERIENCE ADJUSTMENT IN CONTROLLABLE EVENTS

(75) Inventors: Aaron K. Baughman, Silver Spring, MD (US); Jennifer R. Mahle, Washington, DC (US); Peter K. Malkin, Ardsley, NY (US); Russell R. Vane, III, Herndon, VA (US)

(73) Assignee: International Business Machines Corporation, Armonk, NY (US)

( * ) Notice: Subject to any disclaimer, the term of this patent is extended or adjusted under 35 U.S.C. 154(b) by 322 days.

(21) Appl. No.: 13/282,580

(22) Filed: Oct. 27, 2011

(65) Prior Publication Data

US 2013/0110760 A1 May 2, 2013

(51) Int. Cl.
| | |
|---|---|
| G06N 5/02 | (2006.01) |
| A61B 5/16 | (2006.01) |
| A63F 13/30 | (2014.01) |
| A63F 13/40 | (2014.01) |
| A61B 5/0205 | (2006.01) |
| G06F 19/00 | (2011.01) |

(52) U.S. Cl.
CPC ............. *A61B 5/165* (2013.01); *A61B 5/02055* (2013.01); *G06F 19/3431* (2013.01); *A63F 13/12* (2013.01); *A63F 2300/558* (2013.01); *A63F 13/10* (2013.01); *A61B 2560/0252* (2013.01)
USPC .......................................................... 706/52

(58) Field of Classification Search
CPC ... A63F 13/10; A63F 13/12; A63F 2300/558; A61B 5/165; A61B 2560/0252; A61B 5/02055; G06F 19/3475; G06N 5/02
USPC ........................................... 706/52; 345/633
See application file for complete search history.

(56) References Cited

U.S. PATENT DOCUMENTS

| | | | |
|---|---|---|---|
| 6,937,885 B1 | 8/2005 | Lewis et al. | |
| 7,263,213 B2 | 8/2007 | Rowe | |
| 7,263,226 B1 | 8/2007 | Stein | |
| 7,817,833 B2 | 10/2010 | Ramsay et al. | |
| 2006/0053377 A1* | 3/2006 | Newell et al. | ................. 715/744 |

(Continued)

FOREIGN PATENT DOCUMENTS

| | | |
|---|---|---|
| CN | 101853259 A | 10/2010 |
| WO | 2010129074 A1 | 11/2010 |

OTHER PUBLICATIONS

Bostick et al., Instrumental Systematic Errors in a Chromotomographic Hyperspectral Imaging System, AN-11258511, IEEEAC paper #1094, Version 4, 2010, 15 pages.

(Continued)

*Primary Examiner* — Jeffrey A Gaffin
*Assistant Examiner* — Dave Misir
(74) *Attorney, Agent, or Firm* — Douglas A. Lashmit; Hoffman Warnick LLC

(57) ABSTRACT

A method for adjusting a user's experience of a controllable event including determining a user somatic state, using a computer device, from user sensor data collected from at least one physiological sensor; determining a user cognitive state, using the computer device, from user experience data collected from the user; determining a user experience model, using the computer device, from the user somatic state and the user cognitive state; correlating, using the computer device, at least one user hypothesis with the user experience model; and adjusting the controllable event, using the computer device, based upon the at least one user hypothesis.

20 Claims, 3 Drawing Sheets

(56) References Cited

U.S. PATENT DOCUMENTS

| | | |
|---|---|---|
| 2009/0167787 A1* | 7/2009 | Bathiche et al. .............. 345/633 |
| 2009/0171902 A1* | 7/2009 | MacLaurin et al. .............. 707/3 |
| 2009/0248594 A1* | 10/2009 | Castleman et al. ............. 706/11 |
| 2009/0318815 A1 | 12/2009 | Barnes et al. |
| 2010/0208951 A1 | 8/2010 | Williams et al. |
| 2010/0246907 A1 | 9/2010 | Wachman et al. |
| 2010/0250554 A1* | 9/2010 | Shu .............................. 707/748 |

OTHER PUBLICATIONS

Giles Hogben, ENISA Briefing: Behavioural Biometrics, Jan. 2010, 10 pages.

Emilio Mordini, Biometric Identification Technology Ethics, Final Scientific Report, Feb. 2007, 34 pages.

Patent Cooperation Treaty, Notification of Transmittal of the International Search Report and the Written Opinion of the International Searching Authority for PCT/IB2012/055502, dated Mar. 14, 2013, 10 pages.

Cocciolo et al., "Using Social Network Analysis to Highlight an Emerging Online Community of Practice," Jul. 2007, 5 pages, CSCL'07:Proceedings of the 8th International Conference on Computer Supported Collaborative Learning.

Fu et al., "Boosted Band Ratio Feature Selection for Hyperspectral Image Classification," 2006, pp. 1059-1062, 18th International Conference on Pattern Recognition, vol. 1.

Kawsar et al., "A Portable Toolkit for Supporting End-User Personalization and Control in Context-Aware Applications," May 2010, pp. 1-21, Multimedia Tools and Applications, vol. 47 Issue 3.

Kawsar et al., "Persona: A Portable Tool for Augmenting Proactive Applications with Multimodal Personalization Support," Dec. 2007, pp. 160-168, Proceedings MUM.

Martin et al., "Restructuring Activity and Place: Augmented Reality Games on Handhelds," Jun. 2008, 8 pages, Proceedings of the 8th International Conference on International Conference for the Learning Sciences, vol. 2.

Nagapraveen et al., "Flexible Reactive Capabilities in Component-Based Autonomic Systems," 2008,pp. 97-106, Fifth IEEE Workshop on Engineering of Autonomic and Autonomous Systems.

Saidi et al., "Social Learning Applications in Resource Constrained Networks," 2009, pp. 256-262, 2009 International Conf6erence on Computational Science and Engineering.

Yang et al., "Modeling Emotional Action for Social Characters," Dec. 2008, pp. 321-337, The Knowledge of Engineering Review, vol. 23, No. 4.

Zimmermann, "Context-Awareness in User Modelling: Requirements Analysis for a Case-Based Reasoning Application," 2003, pp. 718-732, Proceedings of the 5th international conference on Case-based reasoning: Research and Development.

Zimmermann, "Personalization and Context Management," 2005, pp. 1-29, User Modeling and User-Adapted Interaction, vol. 15 Issue 3-4.

* cited by examiner

USER EXPERIENCE ADJUSTMENT IN CONTROLLABLE EVENTS

FIELD OF THE INVENTION

The present invention relates generally to user experiences, and more particularly to adjusting a user's experience of a controllable event.

BACKGROUND OF THE INVENTION

Users experience a variety of controllable events. Controllable events might include movies (both two and three dimensional), virtual reality (through personal computers, video games, and other computer generated alternative realities), amusement park rides, and a variety of immersive environments. Controllable events may also include riding in an automobile or various forms of mass transportation. If an event may be modulated in any way, then it is a controllable event. Controllable events are becoming pervasive within society. Users, as consumers, expect greater personalization and immersive experiences from controllable events. As controllable events mature within healthcare, entertainment, public service, and a multitude of other areas of our society, products and services may want to produce more personalized experiences for each user.

SUMMARY OF THE INVENTION

In a first aspect, the invention provides a method for adjusting a user's experience of a controllable event, the method comprising: determining a user somatic state, using a computer device, from user sensor data collected from at least one physiological sensor; determining a user cognitive state, using the computer device, from user experience data collected from the user; determining a user experience model, using the computer device, from the user somatic state and the user cognitive state; correlating, using the computer device, at least one user hypothesis with the user experience model; and adjusting the controllable event, using the computer device, based upon the at least one user hypothesis.

In a second aspect, the invention provides a user experience adjustment system, comprising: a computer hardware device including: a somatic system for determining a user somatic state from user sensor data collected from at least one physiological sensor; a cognitive system for determining a user cognitive state from user experience data collected from the user; an experience model system for: determining a user experience model from the user somatic state and the user cognitive state, and correlating at least one user hypothesis with the user experience model; and an adjustment system for adjusting the controllable event based upon the at least one user hypothesis.

In a third aspect, the invention provides a computer program comprising program code embodied in at least one computer-readable medium, which when executed, enables a computer system to implement a method of user experience adjustment, the method comprising: determining a user somatic state from user sensor data collected from at least one physiological sensor; determining a user cognitive state from user experience data collected from the user; determining a user experience model from the user somatic state and the user cognitive state; correlating at least one user hypothesis with the user experience model; and adjusting the controllable event based upon the at least one user hypothesis.

BRIEF DESCRIPTION OF THE DRAWINGS

The above and other objects, features and advantages of the invention will be better understood by reading the following more particular description of the invention in conjunction with the accompanying drawings.

Figure 1:
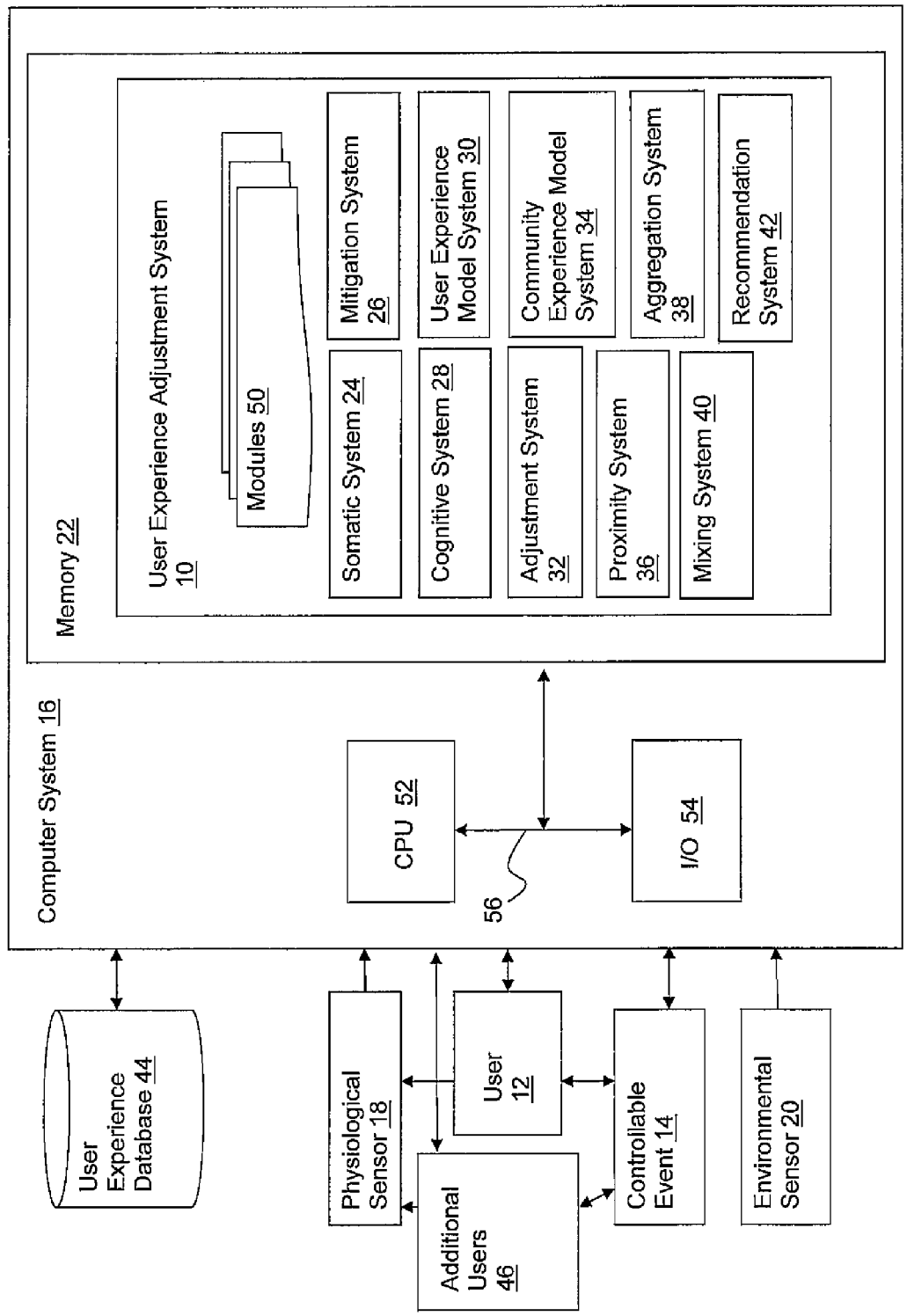
FIG. 1 depicts one embodiment of a user experience adjustment system in accordance with the present invention.

The drawings are not necessarily to scale. The drawings are merely schematic representations, not intended to portray specific parameters of the invention. The drawings are intended to depict only typical embodiments of the invention, and therefore should not be considered as limiting the scope of the invention. In the drawings, like numbering represents like elements.

DETAILED DESCRIPTION OF THE INVENTION

Referring to FIG. 1, an embodiment of a user experience adjustment system 10 in accordance with the present invention is shown. A user 12 may interact with a controllable event 14. Both the user 12 and the controllable event 14 interact with a computer system 16 that includes the user experience adjustment system 10. At least one physiological sensor 18 detects physiological data of the user 12 and provides the physiological data to the computer system 16. At least one environmental sensor 20 detects environmental data and provides the environmental data to the computer system 16. The user experience adjustment system 10 is provided to adjust the user's experience of the controllable event 14. User experience adjustment system 10 may be implemented as a software program product that can be stored in memory 22 and be executed on any type of computer system 16. A person skilled in the art will recognize that the invention may be implemented on one or more computer systems and this disclosure is not intended to limit such potential embodiments. In this illustrative embodiment, user experience adjustment system 10 includes: a somatic system 24, a mitigation system 26, a cognitive system 28, a user experience model system 30, an adjustment system 32, a community experience model system 34, a proximity system 36, an aggregation system 38, a mixing system 40, and a recommendation system 42.

Figure 2:
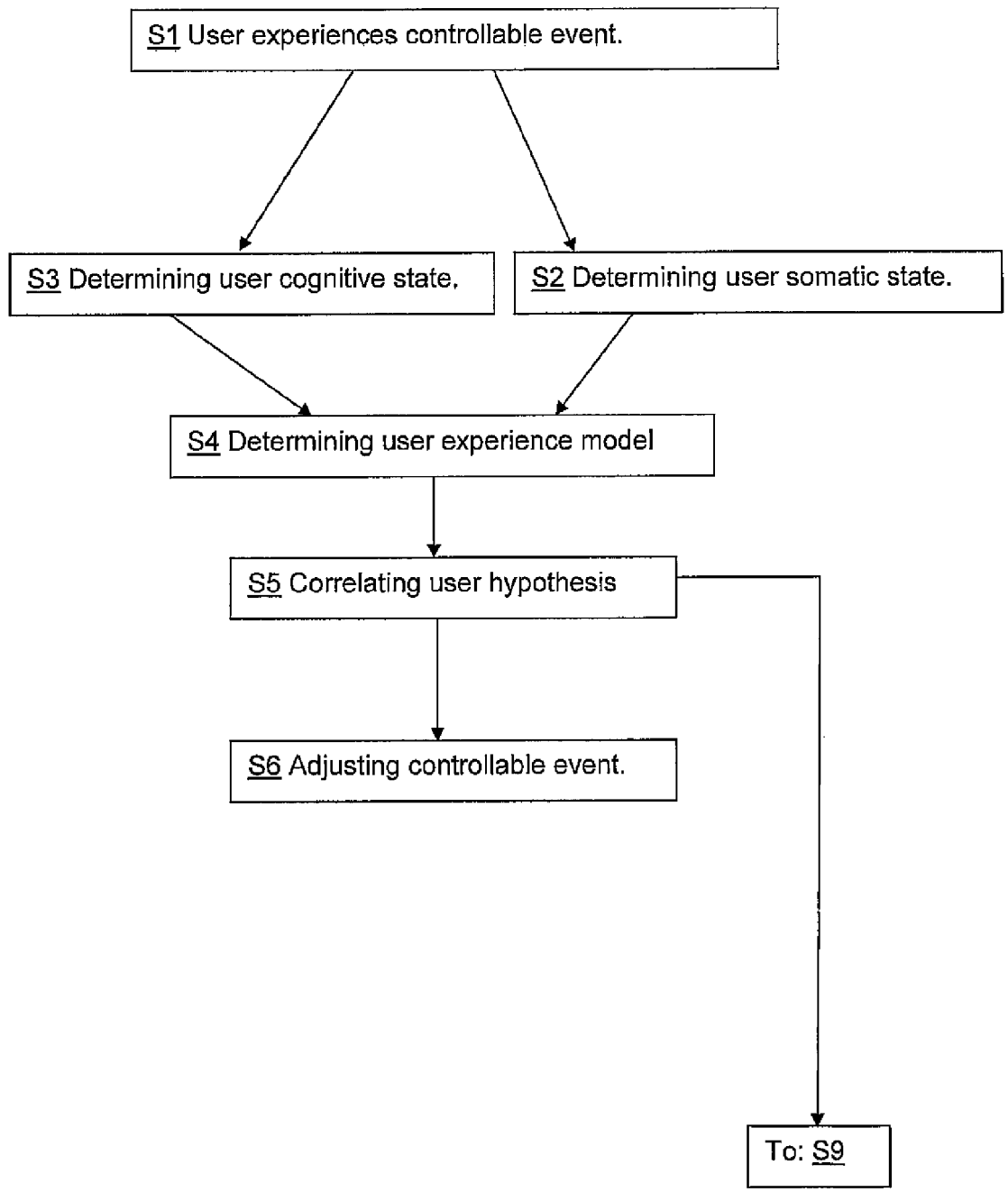
FIG. 2 is a flow chart of one embodiment of a process for user experience adjustment in accordance with the present invention.
Figure 3:
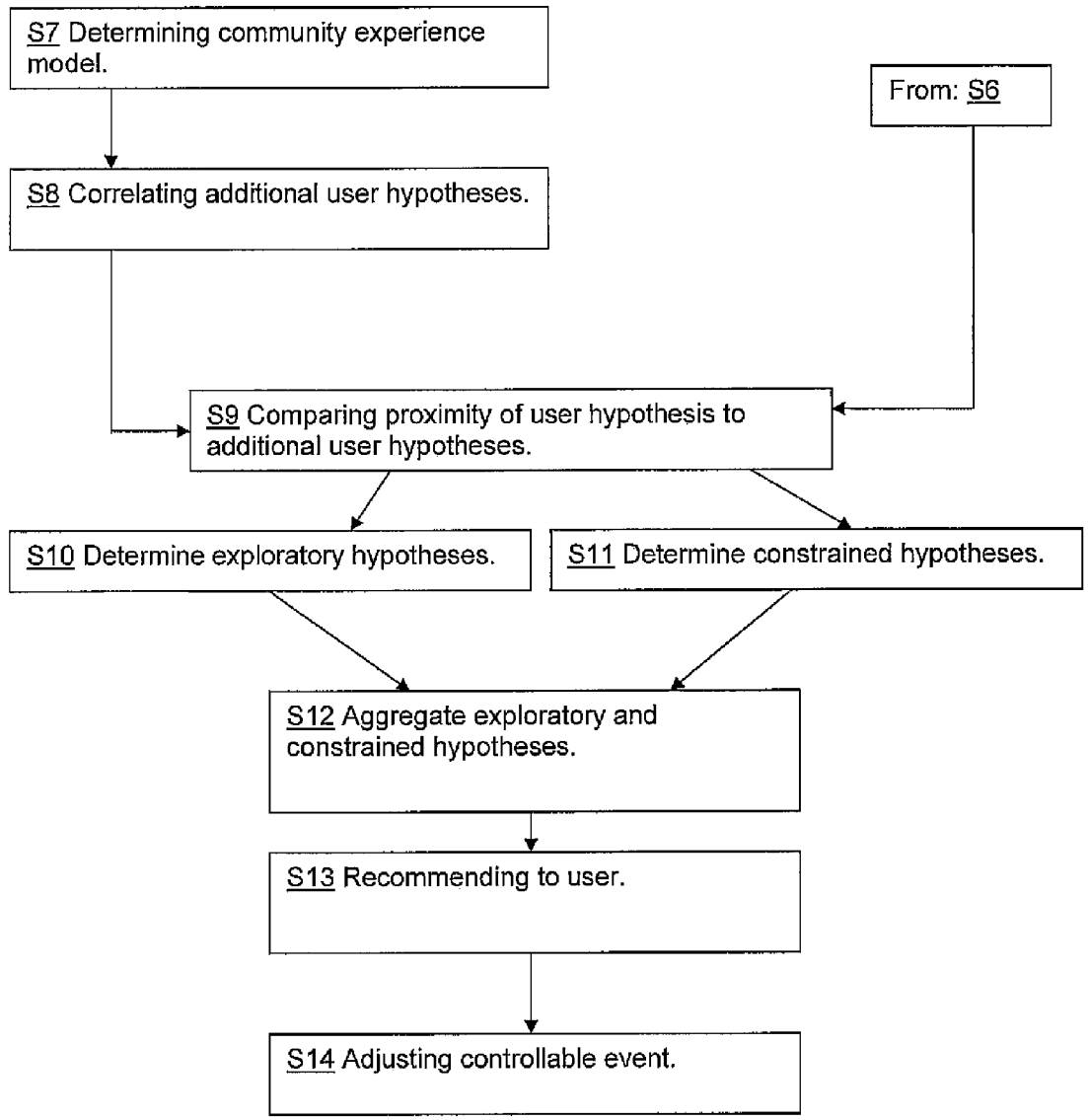
FIG. 3 is a flow chart of one embodiment of a process for user experience adjustment in accordance with the present invention.

Continuing to refer to FIG. 1 and referring to FIGS. 2 and 3, one embodiment of a process for user experience adjustment is shown. At 51 the user 12 experiences the controllable event 14. Experiences may include pre-event experiences, during-event experiences, and post-event experiences of user. Controllable event 14 includes any event that may be modulated in a way that the user's experience of the controllable event 14 is adjusted. Examples include, amusement park rides, movies, video games, virtual realities, immersive environments, building environmental systems, automobiles, and mass transportation. A person skilled in the art will readily recognize many user 12 interactions with controllable events 14. Modulating a controllable event 14 may include adjusting any parameter of the controllable event 14 that is experienced by the user 12. Examples of adjustable parameters may include, temperatures, G-forces, vibration, lighting levels, sound levels, olfactory levels, and other sensory parameters. A person skilled in the art will readily recognize many adjustable parameters for controllable events 14.

At least one physiological sensor 18 may detect physiological data of user 12 such as skin temperature, skin tone, degree of skin moisture (i.e. sweating), body temperature, degree of muscle tension, pupil size, eye movement, sounds, blood pressure, heart rate, respiration rate, brain activity, and any other physiological data of user. Physiological sensor 18 may be a hyperspectral collection device, acoustical collection device, heart rate monitor, spirometer, pupillometer, sphygmomanometer, electroencephalograph, and any other now known or to be developed physiological sensor 18. Physiological sensor 18 may be non-invasive wherein the physiological sensor 18 either does not make contact with the user 12 or does not break the skin of the user 12; or invasive wherein the physiological sensor 18 makes contact by breaking the skin of the user 12. A person skilled in the art will readily recognize that any number of now known or to be developed physiological sensors 18 may be utilized.

In one embodiment, somatic system 24 may receive physiological data from at least one physiological sensor 18. At S2, somatic system 24 may determine a user somatic state. Somatic system 24 may correlate physiological data with experiences of user 12 in interaction with the controllable event 14.

In one embodiment, mitigation system 26 may receive environmental data from at least one environmental sensor 20. Mitigation system 26 may interpret the environmental data and send mitigation data to somatic system 24 to adjust physiological data for environmental factors. For example, environmental data may include ambient temperature of the controllable event 14. Comparatively hot ambient temperatures may saturate infrared wavelength collection. If the ambient temperature is comparatively hot for the user 12 then readings of skin temperature as a measure of the user's experience of the controllable event 14 would be mitigated for the hot ambient temperature. In an embodiment using more than one physiological sensor 18, mitigation system 26 may compare signals from each physiological sensor 18 and may boost one or more of the signals for proportionate measurements. For example, mitigation system 26 may evaluate the quality of each respective signal and band. Mitigation system 26 may boost signal quality proportionately within each modality as well as between each modality.

In one embodiment, cognitive system 28 may receive reports of experience from user 12 in interaction with the controllable event. For example, the user 12 may answer questions on how he or she is feeling before, during, and after an amusement park ride. At S3, cognitive system may determine a user cognitive state.

User experience model system 30 may receive the user cognitive state and the user somatic state. At S4, user experience model system 30 may determine a user experience model for the user 12 based upon the user cognitive state and the user somatic state. For example, user experience model system 30 may correlate a report from the user 12 of being frightened with a specific detected heart rate of the user 12.

At S5, user experience model system 30 may correlate at least one user hypothesis with the user experience model. A plurality of user hypotheses may be stored in a user experience database 44. Each user hypothesis may be a potential experience for a user 12. Each hypothesis may be created from user experience history (i.e., one or more previous user experiences). In one embodiment, each hypothesis may be generated through supervised and offline learning by the user 12. Each previous user experience correlates a previous user cognitive state and a previous user somatic state. For example, after the user 12 experiences each controllable event 14 the user 12 may label the experience. For example, the label may indicate if the user 12 liked the experience or not, whether the experience was frightening or not, pleasing or not, and any other user experience assessments.

At S6, adjustment system 32 may receive at least one user hypothesis and may adjust the controllable event 14 in order to adjust the user's 12 experience of the controllable event 14. Alternatively, user 12 may receive at least one hypothesis and may instruct adjustment system 32 to adjust the user's 12 experience of the controllable event 14.

User experience model, user cognitive state, user somatic state, and user hypotheses may be stored in a user experience database 44. It should be readily apparent that one user 12 may experience a plurality of different controllable events or the same controllable event a plurality of times.

A plurality of additional users 46 may experience a plurality of different controllable events or the same controllable event a plurality of times. For each additional user 46 and each controllable event experienced by each additional user 46, user experience adjustment system 10 may determine and store an additional user experience model, an additional user cognitive state, an additional user somatic state, and at least one additional user hypothesis. At S7, community experience model system 34 may determine one or more community experience models and, at S8, correlate additional user hypotheses with each community experience model.

Proximity system 36 may receive the user hypotheses and the additional user hypotheses. At S9, proximity system 36 compares the user hypotheses with the additional user's hypotheses and, as a result of the comparing, at S10, determines a set of exploratory hypotheses and, at S11, determines a set of constrained hypotheses. Constrained hypotheses may predict similar user experiences and are likely to be experiences that the user 12 is accustomed to. Exploratory hypotheses may predict different user experiences and are likely to be experiences that are new for the user 12.

At S12, aggregation system 38 aggregates hypotheses from the constrained hypotheses and the exploratory hypotheses. In one embodiment, prior to aggregation, mixing system 40 may apply a mixing coefficient to the constrained hypotheses and the exploratory hypotheses. Mixing coefficient may be set by user to reflect the degree the user 12 wants each experience to be adjusted towards exploratory hypotheses or towards constrained hypotheses. For example, the more the user 12 wants to adjust experiences towards predictable and known, then the mixing coefficient would favor constrained hypotheses and the more the user 12 wants to adjust experiences towards adventuresome and unknown, then the mixing coefficient would favor exploratory hypotheses. Aggregate hypotheses with mixes of a larger proportion of constrained hypotheses may be familiar to the user 12. Aggregate hypotheses with mixes of a larger proportion of exploratory hypotheses may be newer to the user 12.

At S13, recommendation system 42 receives the aggregate hypotheses and recommends adjustment to the controlled event based upon the received aggregate hypotheses. User 12 may select a recommendation or recommendation system 42 may select a recommendation based upon a user profile. At S14, adjustment system adjusts the controllable event 14 based on the selected recommendation.

In FIG. 1, computer system 16 includes a user experience adjustment system 10 stored in a memory 22 and described herein. Computer system 16 is shown including a central processing unit (CPU) 52 (e.g., one or more processors), an input/output (I/O) component 54 (e.g., one or more I/O interfaces and/or devices), and a communications pathway 56. In one embodiment, CPU 52 executes program code, such as user experience adjustment system 10, which is at least partially embodied in memory 22. While executing program code, CPU 52 can process data, which can result in reading and/or writing the data to/from memory 22 and/or I/O component 54 for further processing. Communications pathway 56 provides a communications link between each of the components in computer system 16. I/O component 54 can comprise one or more human I/O devices or storage devices, which enable user 12 to interact with computer system 16 and/or one or more communications devices to enable user 12 to communicate with computer system 16 using any type of communications link. To this extent, user experience adjustment system 10 can manage a set of interfaces (e.g., graphical user interface(s), application program interface, and/or the like) that enable human and/or system interaction with user experience adjustment system 10.

In any event, computer system 16 can comprise one or more general purpose computing articles of manufacture (e.g., computing devices) capable of executing program code installed thereon. As used herein, it is understood that "program code" means any collection of instructions, in any language, code or notation, that cause a computing device having an information processing capability to perform a particular function either directly or after any combination of the following: (a) conversion to another language, code or notation; (b) reproduction in a different material form; and/or (c) decompression. To this extent, user experience adjustment system 10 can be embodied as any combination of system software and/or application software. In any event, the technical effect of computer system 16 is to adjust a user's experience of a controllable event.

Further, user experience adjustment system 10 can be implemented using a set of modules 50. In this case, a module 50 can enable computer system 16 to perform a set of tasks used by user experience adjustment system 10, and can be separately developed and/or implemented apart from other portions of user experience adjustment system 10. User experience adjustment system 10 may include modules 50 which comprise a specific use machine/hardware and/or software. Regardless, it is understood that two or more modules 50, and/or systems may share some/all of their respective hardware and/or software. Further, it is understood that some of the functionality discussed herein may not be implemented or additional functionality may be included as part of computer system 16.

When computer system 16 comprises multiple computing devices, each computing device may have only a portion of user experience adjustment system 10 embodied thereon (e.g., one or more modules 50). However, it is understood that computer system 16 and user adjustment system 10 are only representative of various possible equivalent computer systems that may perform a process described herein. To this extent, in other embodiments, the functionality provided by computer system 16 and user experience adjustment system 10 can be at least partially implemented by one or more computing devices that include any combination of general and/or specific purpose hardware with or without program code. In each embodiment, the hardware and program code, if included, can be created using standard engineering and programming techniques, respectively.

Regardless, when computer system 16 includes multiple computing devices, the computing devices can communicate over any type of communications link. Further, while performing a process described herein, computer system 16 can communicate with one or more other computer systems using any type of communications link. In either case, the communications link can comprise any combination of various types of wired and/or wireless links; comprise any combination of one or more types of networks; and/or utilize any combination of various types of transmission techniques and protocols.

As discussed herein, user experience adjustment system 10 enables computer system 16 to provide processing instructions for adjusting a user's experience of a controllable event. User experience adjustment system 10 may include logic, which may include the following functions: somatic system 24, mitigation system 26, cognitive system 28, user experience model system 30, adjustment system 32, community experience model system 34, proximity system 36, aggregation system 38, mixing system 40, and recommendation system 42. In one embodiment, user experience adjustment system 10 may include logic to perform the above-stated functions. Structurally, the logic may take any of a variety of forms such as a field programmable gate array (FPGA), a microprocessor, a digital signal processor, an application specific integrated circuit (ASIC) or any other specific use machine structure capable of carrying out the functions described herein. Logic may take any of a variety of forms, such as software and/or hardware. However, for illustrative purposes, user experience adjustment system 10 and logic included therein will be described herein as a specific use machine. As will be understood from the description, while logic is illustrated as including each of the above-stated functions, not all of the functions are necessary according to the teachings of the invention as recited in the appended claims.

While shown and described herein as user experience adjustment system 10, it is understood that aspects of the invention further provide various alternative embodiments. For example, in one embodiment, the invention provides a computer program embodied in at least one computer-readable medium, which when executed, enables a computer system to adjust a user's experience of a controllable event. To this extent, the computer-readable medium includes program code, such as user experience adjustment system 10, which implements some or all of a process described herein. It is understood that the term "computer-readable medium" comprises one or more of any type of tangible medium of expression capable of embodying a copy of the program code (e.g., a physical embodiment). For example, the computer-readable medium can comprise: one or more portable storage articles of manufacture; one or more memory/storage components of a computing device; paper; and/or the like.

In still another embodiment, the invention provides a method of determining and correcting errors and recovering the step in the asynchronous work process. In this case, a computer system, such as computer system 16 (FIG. 1), can be obtained (e.g., created, maintained, made available, etc.) and one or more modules 50 for performing a process described herein can be obtained (e.g., created, purchased, used, modified, etc.) and deployed to the computer system. To this extent, the deployment can comprise one or more of: (1) installing program code on a computing device from a computer-readable medium; (2) adding one or more computing and/or I/O devices to the computer system; and (3) incorporating and/or modifying the computer system to enable it to perform a process described herein.

It is understood that aspects of the invention can be implemented as part of a business method that performs a process described herein on a subscription, advertising, and/or fee basis. That is, a service provider could offer to provide processing instructions for adjusting a user's experience of a controllable event as described herein. In this case, the service provider can manage (e.g., create, maintain, support, etc.) a computer system, such as computer system 16 (FIG. 1), that performs a process described herein for one or more customers. In return, the service provider can receive payment from the customer(s) under a subscription and/or fee agreement, receive payment from the sale of advertising to one or more third parties, and/or the like.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A method for adjusting a user's experience of a controllable event, the method comprising:
    determining a user somatic state, using a computer device, from user sensor data collected from at least one physiological sensor;
    determining a user cognitive state, using the computer device, from user experience data collected from the user;
    determining a user experience model, using the computer device, from the user somatic state and the user cognitive state;
    correlating, using the computer device, at least one user hypothesis with the user experience model, wherein the at least one user hypothesis is a potential user experience and is created from at least one different previous user experience, and wherein the at least one different previous user experience correlates the different previous user cognitive state and the different previous user somatic state; and
    adjusting the controllable event, using the computer device, based upon the at least one user hypothesis.

2. The method of claim 1, further comprising:
    determining a set of constrained hypotheses by comparing the at least one user hypothesis with a set of additional user hypotheses, wherein each constrained hypothesis predicts a similar user experience; and
    determining a set of exploratory hypotheses by comparing the at least one user hypothesis with a set of additional user hypotheses, wherein each exploratory hypothesis predicts a different user experience.

3. The method of claim 2, further comprising:
    aggregating the set of constrained hypotheses and the exploratory hypotheses; and
    generating a recommendation for the user based upon the aggregating.

4. The method of claim 3, further comprising:
    receiving a mixing coefficient for the aggregating.

5. The method of claim 4, wherein the mixing coefficient determines proportions of the constrained hypotheses and the exploratory hypotheses for the aggregating.

6. The method of claim 1, wherein the at least one user hypothesis is determined from a user experience history.

7. The method of claim 1, further comprising:
    mitigating user sensor data for environmental factors.

8. A user experience adjustment system, comprising:
    a computer hardware device including:
    a somatic system for determining a user somatic state from user sensor data collected from at least one physiological sensor;
    a cognitive system for determining a user cognitive state from user experience data collected from the user;
    an experience model system for:
        determining a user experience model from the user somatic state and the user cognitive state, and
        correlating at least one user hypothesis with the user experience model, wherein the at least one user hypothesis is a potential user experience and is created from at least one different previous user experience, and wherein the at least one different previous user experience correlates the different previous user cognitive state and the different previous user somatic state; and
    an adjustment system for adjusting the controllable event based upon the at least one user hypothesis.

9. The system of claim 8, further comprising:
    a proximity system for:
        determining a set of constrained hypotheses by comparing the at least one user hypothesis with a set of additional user hypotheses, wherein each constrained hypothesis predicts a similar user experience, and
        determining a set of exploratory hypotheses by comparing the at least one user hypothesis with a set of additional user hypotheses, wherein each exploratory hypothesis predicts a different user experience.

10. The system of claim 9, further comprises:
    an aggregation system for aggregating the set of constrained hypotheses and the exploratory hypotheses; and
    a recommendation system for generating a recommendation for the user based upon the aggregating.

11. The system of claim 10, wherein the adjustment system includes receiving a mixing coefficient for the aggregating.

12. The system of claim 11, wherein the mixing coefficient determines proportions of the constrained hypotheses and the exploratory hypotheses for the aggregating.

13. The system of claim 8, wherein the at least one user hypothesis is determined from a user experience history.

14. The system of claim 8, further comprising:
    a mitigation system for mitigating user sensor data for environmental factors.

15. A computer program comprising program code embodied in at least one non-transitory computer-readable medium, which when executed, enables a computer system to implement a method of adjusting a user's experience of a controllable event, the method comprising:
    determining a user somatic state from user sensor data collected from at least one physiological sensor;
    determining a user cognitive state from user experience data collected from the user;
    determining a user experience model from the user somatic state and the user cognitive state;
    correlating at least one user hypothesis with the user experience model, wherein the at least one user hypothesis is a potential user experience and is created from at least one different previous user experience, and wherein the at least one different previous user experience correlates the different previous user cognitive state and the different previous user somatic state; and adjusting the controllable event based upon the at least one user hypothesis.

16. The program product of claim 15, further comprising:

determining a set of constrained hypotheses by comparing the at least one user hypothesis with a set of additional user hypotheses, wherein each constrained hypothesis predicts a similar user experience; and determining a set of exploratory hypotheses by comparing the at least one user hypothesis with a set of additional user hypotheses, wherein each exploratory hypothesis predicts a different user experience.

17. The program product of claim 16, further comprising:

aggregating the set of constrained hypotheses and the exploratory hypotheses; and generating a recommendation for the user based upon the aggregating.

18. The program product of claim 17, further comprising:
receiving a mixing coefficient for the aggregating.

19. The program product of claim 18, wherein the mixing coefficient determines proportions of the constrained hypotheses and the exploratory hypotheses for the aggregating.

20. The program product of claim 15, further comprising:
mitigating user sensor data for environmental factors.

\* \* \* \* \*